United States Patent [19]

Konishi

[11] Patent Number: 4,461,724

[45] Date of Patent: Jul. 24, 1984

[54] PEPTIDE COMPOUNDS, A PROCESS FOR MANUFACTURING THEM, PHARMACEUTICAL COMPOSITIONS CONTAINING THEM, AND METHODS FOR TREATING ULCER AND THROMBUS WITH THEM

[75] Inventor: Jin-emon Konishi, Musashino, Japan

[73] Assignee: Nippon Zoki Pharmaceutical Co., Ltd., Osaka, Japan

[21] Appl. No.: 435,974

[22] Filed: Oct. 22, 1982

[30] Foreign Application Priority Data

Oct. 28, 1981 [JP] Japan .................................. 56-172515
Sep. 14, 1982 [JP] Japan .................................. 57-160138

[51] Int. Cl.³ ............................................ C07C 103/52
[52] U.S. Cl. .............................................. 260/112.5 R
[58] Field of Search ................................. 260/112.5 R

[56] References Cited

U.S. PATENT DOCUMENTS 4,171,299 10/1979 Hamburger ................. 260/112.5 R

*Primary Examiner*—Delbert R. Phillips
*Attorney, Agent, or Firm*—Quaintance & Murphy

[57] ABSTRACT

Novel peptides having the general formula (I):

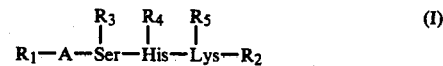

wherein A denotes an amino acid residue which may optionally have protecting group; $R_1$ denotes hydrogen atom, lower alkyl group, acyl group, alkoxycarbonyl group, or aralkyloxycarbonyl group which may optionally be substituted with halogen atom, alkoxy group, or nitro group; $R_2$ denotes hydroxy group, alkoxy group, aryloxy group, aralkyloxy group, or amiono group which may optionally be substituted with lower alkyl group; $R_3$ denotes hydrogen atom, lower alkyl group, acyl group, or aralkyl group; $R_4$ denotes hydrogen atom, tosyl group, trityl group, aralkyl group, or aralkyloxycarbonyl group which may optionally be substituted with halogen atom, alkoxy group, or nitro group; $R_5$ denotes hydrogen atom, lower alkyl group, acyl group, tosyl group, alkoxycarbonyl group, or aralkyloxycarbonyl group which may optionally be substituted with halogen atom, alkoxy group, or nitro group; and pharmaceutically acceptable salts; a process for manufacturing them; pharmaceutical compositions containing them as active ingredient; and a method for treating ulcer and thrombus therewith.

19 Claims, No Drawings

PEPTIDE COMPOUNDS, A PROCESS FOR MANUFACTURING THEM, PHARMACEUTICAL COMPOSITIONS CONTAINING THEM, AND METHODS FOR TREATING ULCER AND THROMBUS WITH THEM

DETAILED DESCRIPTION OF THE INVENTION

The present invention relates to novel peptide compounds and pharmaceutically acceptable salts thereof, a process for manufacturing them, pharmaceutical compositions containing them as active ingredient, and method for treating ulcer and thrombus with them.

Recently various peptides and their derivatives have been so far synthesized, and their actions on the organism have been examined. Upon strenuously having made the study, the present inventor has found out novel peptide compounds effective as medicine which have excellent antiulcer action and antithrombotic action with pharmaceutically low toxicity, and thus accomplished the present invention.

Accordingly, an object of the present invention is to provide novel peptide compounds useful as medicine.

Another object of the present invention is to provide a method for manufacturing such novel peptide compounds.

Still another object of the present invention is to provide pharmaceutical compositions containing such novel peptide compounds as active ingredient.

Further object of the present invention is to provide a method for treating ulcer and thrombus with such novel peptide compounds.

The novel peptide compounds according to the present invention have the following general formula (I):

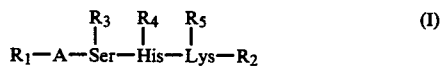

wherein A denotes an amino acid residue which may optionally have protecting group; $R_1$ denotes hydrogen atom, lower alkyl group, acyl group, alkoxycarbonyl group, or aralkyloxycarbonyl group which may optionally be substituted with halogen atom, alkoxy group, or nitro group; $R_2$ denotes hydroxy group, alkoxy group, aryloxy group, aralkyloxy group, or amino group which may optionally be substituted with lower alkyl group; $R_3$ denotes hydrogen atom, lower alkyl group, acyl group, or aralkyl group; $R_4$ denotes hydrogen atom, tosyl group, trityl group, aralkyl group, or aralkyloxycarbonyl group which may optionally be substituted with halogen atom, alkoxy group, or nitro group; $R_5$ denotes hydrogen atom, lower alkyl group, acyl group, tosyl group, alkoxycarbonyl group, or aralkyloxycarbonyl group which may optionally be substituted with halogen atom, alkoxy group, or nitro group.

The peptides and amino acids in the present application are expressed by the abbreviations adopted by IUPAC and IUB or by the abbreviations commonly used in the art to which the present invention pertains.

For example, the following abbreviations are used.
Ser: Serine
His: Histidine
Lys: Lysine
Gly: Glycine
Ala: Alanine
Sar: N-Methylglycine (Sarcosine)
Val: Valine
Leu: Leucine
Ileu: Isoleucine
Thr: Threonine
Pro: Proline
Hyp: Hydroxyproline
(pry)Glu: Pyroglutamic acid
Glu: Glutamic acid
Gln: Glutamine
Asn: Asparagine
Asp: Aspartic acid
Phe: Phenylalanine
Tyr: Tyrosine
DOPA: Dihyoxyphenylalanine
Trp: Tryptophane The amino acid residues in this invention may be any of the D-isomer, L-isomer and DL-isomer (Racemic mixture).

In the above formula (I), A may be an amino acid which may optionally have one or more protecting groups, for example, an α-amino acid which constitutes protein, and is preferably Gly, Ala, Sar, Val, Leu, Ileu, Ser, Thr, Pro, Hyp, (pyr)Glu, Glu, Gln, Asn, Asp, Phe, Tyr, DOPA, Trp etc., and as the protecting group, any protecting group of amino acid employed in conventional peptide synthesis may be employed.

$R_1$ may be hydrogen atom; straight-chain or branched-chain lower alkyl group of 1–6 carbon atoms such as methyl group, ethyl group, propyl group, butyl group, pentyl group, hexyl group; aliphatic or aromatic acyl group such as acetyl group, propionyl group, butyryl group, benzoyl group; alkoxycarbonyl group such as t-butoxycarbonyl group, t-pentyloxycarbonyl group; aralkyloxycarbonyl group which may optionally be substituted with halogen atom, alkoxy group or nitro group, such as benzyloxycarbonyl group, o-chlorobenzyloxycarbonyl group, p-methoxybenzyloxycarbonyl group, p-nitrobenzyloxycarbonyl group; or a protecting group conventionally employed in peptide synthesis.

$R_2$ may be hydroxy group, straight-chain or branched-chain alkoxy group of 1–6 carbon atoms such as methoxy group, ethoxy group, propoxy group, butoxy group, pentyloxy group, hexyloxy group; aryloxy group such as phenoxy group; aralkyloxy group such as benzyloxy group; amino group which may be mono- or di-substituted with lower alkyl group of 1–6 carbon atoms as described for $R_1$; or a protecting group conventionally employed in peptide synthesis.

$R_3$, which indicates the substituents of the hydrogen atom of β-hydroxy group of Ser, may be hydrogen atom, lower alkyl group of 1–6 carbon atoms as recited for $R_1$, such as t-butyl group, acyl group or aralkyl group, such as benzyl group, or a protecting group conventionally employed in peptide synthesis.

$R_4$, which indicates the substituents of the hydrogen atom of β-imidazoyl group of His, may be hydrogen atom, tosyl group, torityl group, aralkyl group, or aralkyloxycarbonyl group (which may be optionally substituted with halogen atom, alkoxy group or nitro group) as recited for $R_1$, or a protecting group conventionally employed in peptide chemistry.

$R_5$, which indicates the substituents of the hydrogen atom of ε-amino group of Lys, may be hydrogen atom, lower alkyl group of 1–6 carbon atoms as recited for $R_1$, acyl group, tosyl group, alkoxycarbonyl group, aralkyloxycarbonyl (which may be optionally substituted with halogen atom, alkoxy group, or nitro group) such as benzyloxy carbonyl group, or a protecting group conventionally employed in peptide chemistry.

A preferred subclass of peptides of the present invention are those of the general formula (II):

$$R_1-A-Ser(Bzl)-His(Tos)-Lys(Z)-OBzl \qquad (II)$$

wherein $R_1$ is hydrogen or Z; and A is a residue of an amino acid selected from the group consisting of Gly, Ala, D-Ala, Leu, Tyr(Bzl), Sar, Pro, (pyr)Glu and Trp.

Another preferred subclass of peptides are those of the general formula (III):

$$R_1-A-Ser(Bzl)-His-Lys(Z)-OBzl \qquad (III)$$

wherein $R_1$ is hydrogen or Z; and A is a residue of an amino acid selected from the group consisting of Gly, Ala, D-Ala, Leu, Tyr(Bzl), Sar, Pro, (pyr)Glu and Trp.

Still another preferred subclass of peptides are unsubstituted peptides of the general formula (IV):

$$A-Ser-His-Lys \qquad (IV)$$

wherein A is a residue of an amino acid selected from the group consisting of Gly, Ala, D-Ala, Leu, Tyr, Sar, Pro, (pyr)Glu and Trp.

The peptide compound of the invention also include pharmaceutically acceptable salts of the compounds of the above formula (I), for example, salts as acid adduct with inorganic acids such as hydrochloric acid, sulfuric acid, nitric acid, hydrobromic acid, phosphoric acid, perchloric acid, thiocyanic acid, boric acid etc. or with organic acids such as formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid, sulfanilic acid etc., and salts with metals such as alkali metals, e.g. sodium, potassium, lithium etc., alkaline earth metals, e.g. calcium, magnesium etc., and aluminum etc.

The peptide compounds of this invention may also include their metal complexes, for example complexes with zinc, nickel, cobalt, copper, iron etc.

These salts and metal complexes may be produced from free peptide compounds in the usual way or may be interchanged with each other.

The peptide compounds according to this invention may be produced by conventional processes in peptide chemistry, and either the solution method or the solid phase synthesis may be employed.

The coupling method for forming a peptide bond may include the azide method, activated ester method, mixed acid anhydride method, acid chloride method, method employing a coupling reagent etc., and they may be employed either alone or in combination according to the necessity.

As amino acid or peptide used as the starting material or materials in the coupling reaction, there are employed those having an appropriate substituent constituting peptide compounds of this invention and/or a protecting group conventionally employed in peptide chemistry. Further, any carboxyl group or amino groups which do not participate in the reaction may be protected by a known method, or any carboxyl group or amino group which participates in the reaction may be activated. For example, there are employable, as starting material, amino acids or their α-amino groups not participating in the condensation reaction which are substituted with alkoxycarbonyl group or aralkyloxycarbonyl group optionally substituted with halogen atom, alkoxy group, nitro group, preferably benzyloxycarbonyl group among the substituents for $R_1$; alkoxy group, aryloxy group or aralkyloxy group, preferably benzyloxy group among the substituents of $R_2$; lower alkyl group or aralkyl group upon necessity, preferably benzyl group among the substituents of $R_3$; tosyl group, trityl group, aralkyl group or aralkyloxycarbonyl group optionally substituted with halogen atom, alkoxy group or nitro group upon necessity, preferably tosyl group or benzyloxymethyl group among the substituents of $R_4$; alkoxycarbonyl group, tosyl group, aralkyloxycarbonyl group optionally substituted with halogen atom, alkoxy group or nitro group upon necessity, preferably benzyloxycarbonyl group among the substituents of $R_5$.

These substituents may be selectively or entirely removed by the conventional method such as catalytic reduction, acidolysis etc. either in the course of the synthetic process of the peptide compound of this invention or in its final stage. Further, if necessary, it is also possible to introduce a substituent which constitutes other peptide compound of this invention by conventional method.

One example of the outline of the production steps of the peptide compounds of this invention is illustrated below, but it should be noted that this invention is not limited thereto.

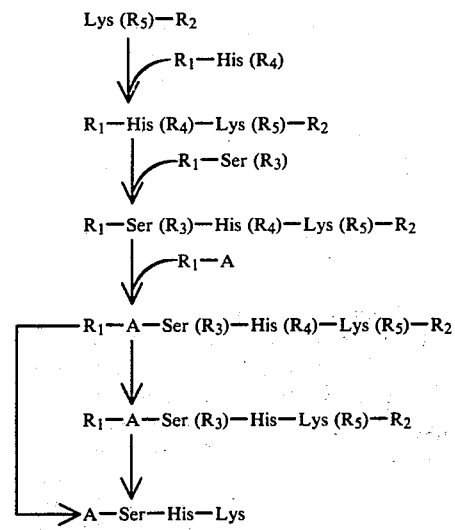

For coupling, various known coupling methods may be employed. For example, such coupling reagents as dicyclohexylcarbodiimide may be employed. In such a case, the reaction may be achieved by stirring at −20° C. to room temperature for one to several hours. While the solvent is preferably inert to both starting materials and product, and preferably dissolves both, suspending conditions can be employed instead; preferable examples being methylene chloride, dimethylformamide, tetrahydrofuran etc.

The peptide compounds of this invention may also be produced in the solid phase synthesis. That is, using an appropriate resin employed in peptide synthesis, for example, chloromethylated or aminomethylated resin, the amino acids or peptides having the aforesaid substituents upon necessity are successively and repeatedly added to synthesize the desired product. For separating the peptide compounds of this invention from the resin, a known method may be employed. When hydrogen fluoride is employed for this purpose, any substituent bound to the constituting amino acid residues may be simultaneously removed.

The peptide compounds of this invention may be isolated and purified in conventional manner. It is desirable to make purification in each coupling step. A strongly acidic ion exchange resin or a resin having adsorbing, distribution or molecular seive effect is useful for isolation and purification of the peptide compounds of this invention.

The obtained products are identified by melting point, TLC, specific rotation, IR, NMR, amino acid analysis, elementary analysis etc.

The production of the peptide compounds of this invention is more particularly illustrated in the following examples. In the examples, the amino acids used are in the L-form unless otherwise stated. The abbreviations used for the substitutes, reagents etc. are as follows:

Z: Benzyloxycarbonyl group
Z-Cl: o-Chlorobenzyloxycarbonyl group
Boc: t-Butoxycarbonyl group
Tos: Tosyl (p-Toluenesulfonyl) group
Bzl: Benzyl group
OBzl: Benzyloxy group
TosOH: p-Toluenesulfonic acid
DCHA: Dicyclohexylamine
DCC: Dicyclohexylcarbodiimide
DMF: Dimethylformamide
AcOH: Acetic acid
TFA: Trifluoroacetic acid
MeOH: Methanol
DMSO: Dimethylsulfoxide In TLC, silica gel was used as a stationary phase and the following solvent systems were employed.
(a) Ethyl acetate:n-hexane=2:1
(b) Chloroform:methanol:water=8:3:1 (lower layer)
(c) Ethyl acetate
(d) n-Butanol:water:acetic acid:pyridine=42:30:24:4
(e) Phenol:water:28% ammonia water=775:215:104
(f) n-Butanol:water:acetic acid=6:2:1
(g) Chloroform:n-hexane:methanol=10:5:1
(h) Chloroform:methanol:acetic acid=95:5:3

The NMR was meaasured using TMS (tetramethylsilane) or TSP-d$_4$ [3-(trimethylsilyl)propionic acid-d$_4$·sodium salt] as the internal standard and expressed in the $\delta$ value.

EXAMPLE 1

(i) 76.3 g of Lys(Z)-OBzl.TosOH and 63.3 g of Boc-His(TOS). DCHA were suspended in 800 ml of tetrahydrofuran, and 32.0 g of DCC was added to the suspension. Then, the mixture was stirred at −10° C. to −15° C. for 2 hours, then at 0° C. for 6 hours, and at room temperature for 10 hours. Thereafter, insoluble substance was filtered off, and the solvent was distilled off. Ethyl acetate was added to the residue, which was then washed with citric acid aqueous solution, saturated saline and sodium bicarbonate aqueous solution, and dried over sodium sulfate anhydride. Then, the solvent was distilled off. The resultant oily matter was solidified by adding ether. The solidified product was washed with ether and dried to obtain 91.0 g of crystals of Boc-His(Tos)-Lys(Z)-OBzl.

(ii) Alternatively, the above compound may also be synthesized by the following process:

That is, 113 g of Boc-His(Tos)-Lys(Z)-OBzl was obtained from 86.8 g of Lys(Z)-OBzl.TosOH and 100 g of Boc-His(Tos).DCHA by employing methylene chloride as the solvent in the above example.
m.p.: 81°-83° C.
TLC: Rf=0.64 (a), 0.81 (b); 0.64 (g), 0.68 (h).
$[\alpha]_D^{15} = -1.40°$ (c=2.1, DMF).

| Elementary Analysis: (C$_{39}$H$_{47}$O$_9$N$_5$S) | | | |
|---|---|---|---|
| | C % | H % | N % |
| Calculated | 61.48 | 6.22 | 9.19 |
| Found | 61.44 | 6.21 | 8.93 |

(iii) 5.0 g of Boc-His(Tos)-Lys(Z)-OBzl was added to 9.8 g of TosOH.H$_2$O dissolved in 26 of dioxane, which was then left at room temperature for an hour with occasional shaking. Next, water was added to it and the mixture was extracted with ethyl acetate. The extract was washed with sodium bicarbonate aqueous solution and saturated saline, and dried over sodium sulfate anhydride. Thereafter, the solvent was distilled off to obtain 3.75 g of His(Tos)-Lys(Z)-OBzl as a pale brown oily matter.

(iv) Alternatively, the above compound may also be synthesized by the following process:

160 ml of TFA was added to 86 g of Boc-His(Tos)-Lys(Z)-OBzl dissolved in 100 ml of ethylene chloride under cooling with ice, and the mixture was stirred at the same temperature for 30 minutes and at room temperature for an hour. The solvent and TFA were distilled off, chloroform was added to the residue, and neutralization was carried out with aqueous potassium carbonate. After the reaction mixture was washed with saturated saline, passed through silica gel and sodium sulfate anhydride columns, the solvent was distilled off. Then, methanol was added to precipitate crystals, which were filtered out and dried to obtain 61.2 g of His(Tos)-Lys(Z)-OBzl. (By this process, the product is obtained in the crystallized form).
m.p.: 79°-80° C.
TLC: Rf=0.64 (f), 0.25 (g), 0.33 (h).
$[\alpha]_D^{20} = -8.40°$ (c=2, DMF).

| Elementary Analysis: (C$_{34}$H$_{39}$O$_7$N$_5$S) | | | |
|---|---|---|---|
| | C % | H % | N % |
| Calculated | 61.71 | 5.94 | 10.58 |
| Found | 61.52 | 5.96 | 10.35 |

(v) A mixture of 1.67 g of Boc-Ser(Bzl), 3.75 g of His(Tos)-Lys(Z)-OBzl and 13.2 ml of methylene chloride was cooled to −15° C., and 1.28 g of DCC was added to the mixture under stirring. Two hours later, the mixture was further stirred at room temperature for 2 hours. Insoluble matters were filtered off and washed with ethyl acetate. The filtrate and the washing were combined and washed with aqueous citric acid, saturated saline and sodium bicarbonate aqueous solution, dried over sodium sulfate anhydride. Then, the solvent was distilled off. The resultant oil residue was crystallized by adding ether to obtain 4.2 g of Boc-Ser(Bzl)-His(Tos)-Lys(Z)-OBzl.
m.p.: 86°-88° C.
TLC: Rf=0.21 (a), 0.83 (b), 0.83 (c), 0.57 (g), 0.62 (h).
$[\alpha]_D^{23} = -4.95°$ (c=2,DMF).
IR (KBr, cm$^{-1}$): 3300, 1740, 1720, 1690, 1640, 1530

NMR (CDCl$_3$): δ=0.9–1.81 (m,6H), 1.41 (s,9H), 2.39 (s,3H), 2.8–3.3 (m,4H), 3.4–3.9 (m,2H), 4.1–4.8 (m,3H), 4.46 (s,2H), 5.05 (brs,4H), 5.42 (brd,1H), 6.98 (brs,1H), 7.0–7.4 (m,19H), 7.70 (d,1H), 7.71 (d,2H), 7.94 (d,1H).

| Elementary Analysis: (C$_{49}$H$_{58}$O$_{11}$N$_6$S) | | | |
|---|---|---|---|
| | C % | H % | N % |
| Calculated | 62.67 | 6.23 | 8.95 |
| Found | 62.53 | 6.07 | 8.71 |

(vi) Alternatively, the above compound may also be synthesized by the following process:

A solution of 19.6 g of DCC in 20 ml of methylene chloride was added to a solution of 21.8 g of Boc-Ser(Bzl) in 80 ml of methylene chloride at −15° C., and stirred for 20 minutes. A solution of 59.6 g of His(Tos)-Lys(Z)-OBzl in 150 ml of methylene chloride was added thereto at −10° C. or below, and stirred for an hour. The precipitates were removed by filtration, and the filtrate was concentrated and ethyl acetate was added thereto. The reaction mixture was then washed with citric acid aqueous solution, saturated saline, sodium bicarbonate aqueous solution and saturated saline, passed through silica gel and sodium sulfate anhydride columns. Thereafter, the solvent was distilled off. Then, ether was added to precipitate crystals, which were filtered out and dried to obtain 78.5 g of powdery crystals of Boc-Ser(Bzl)-His(Tos)-Lys(Z)-OBzl.

EXAMPLE 2

1.5 g of TosOH.H$_2$O dissolved in 4 ml of dioxane was added to 1.0 g of Boc-Ser(Bzl)-His(Tos)-Lys(Z)-OBzl, which was then shaken at room temperature for 40 minutes. After water was added to it, the mixture was extracted with ethyl acetate. The extract was washed with sodium bicarbonate aqueous solution and saturated saline, and dried over sodium sulfate anhydride. Thereafter, the solvent was distilled off. The residue was crystallized by adding ether to obtain 0.75 g of a white powder of Ser(Bzl)-His(Tos)-Lys(Z)-OBzl (Compound 1).

m.p.: 133°–136° C.
TLC: Rf=0.68 (b), 0.24 (g), 0.26 (h)
$[α]_D^{23}$ = +0.4° (c=2, DMF)
IR (KBr, cm$^{-1}$): 3380, 3280, 1720, 1710, 1645, 1540, 1510
NMR (DMSO-d$_6$): δ=1.0–1.9 (m,6H), 2.35 (s,3H), 2.6–3.1 (m,6H), 3.42 (brs,2H), 3.2–3.5 (m,1H), 4.0–4.8 (m,2H), 4.43 (s,2H), 5.00 (s,2H), 5.10 (s,2H), 6.9–7.5 (m,20H), 7.85 (d,2H) 8.15–8.4 (m,2H)

| Elementary Analysis: (C$_{44}$H$_{50}$O$_9$N$_6$S) | | | |
|---|---|---|---|
| | C % | H %. | N % |
| Calculated | 62.99 | 6.01 | 10.02 |
| Found | 62.88 | 5.96 | 10.04 |

(ii) Alternatively, the above compound may also be synthesized by the following process:

150 ml of TFA was added to 87.7 g of Boc-Ser(Bzl)-His(Tos)-Lys(Z)-OBzl dissolved in 130 ml of methylene chloride under cooling with ice, and the mixture was stirred at the same temperature for an hour and then at room temperature for an hour. Thereafter, procedures similar to those in (iv) in Example 1 were conducted to obtain 75.5 g of Compound 1.

EXAMPLE 3

(i) After a mixed solution of 16.45 g of Z-Gly and 60 g of Ser(Bzl)-His(Tos)-Lys(Z)-OBzl (Compound 1) in 314 ml of methylene chloride was cooled to −15° C., 16.23 g of DCC was added to it under stirring. Stirring was continued at the same temperature for 2 hours and then at room temperature. The precipitates were filtered off and washed with methylene chloride. The filtrate and the washing were combined and washed with citric acid aqueous solution, saturated saline and sodium bicarbonate aqueous solution, and dried over sodium sulfate anhydride. Then, the solvent was distilled off. The resultant oily matter was crystallized by adding ethyl acetate to obtain 60.2 g of a white powder of Z-Gly-Ser(Bzl)-His(Tos)-Lys(Z)-OBzl (Compound 2).

m.p.: 144°–145.5° C. TLC: Rf=0.03 (a), 0.82 (b), 0.73 (c), 0.35 (g), 0.53 (h).
$[α]_D^{23}$ = −6.2° (c=2, DMF).
IR (KBr, cm$^{-1}$): 3450, 3300, 1735, 1690, 1660, 1635, 1540, 1515.
NMR (CDCl$_3$+CD$_3$OD): δ=1.0–1.9 (m,6H), 2.39 (s,3H), 2.85–3.2 (m,4H), 3.5–3.9 (m,2H), 3.85 (brs,2H), 4.2–4.8 (m,3H), 4.48 (s,2H), 5.03 (s,2H), 5.06 (s,2H), 5.10 (s,2H), 7.0–7.5 (m,23H), 7.76 (d,2H), 7.91 (d,1H).

| Elementary Analysis: (C$_{54}$H$_{59}$O$_{12}$N$_7$S) | | | |
|---|---|---|---|
| | C % | H % | N % |
| Calculated | 62.96 | 5.77 | 9.52 |
| Found | 62.78 | 5.69 | 9.58 |

(ii) A solution of 8.1 g of DCC in 40 ml of methylene chloride was added to 8.2 g of Z-Gly suspended in 100 ml of methylene chloride at −10° C. or below, and the mixture was stirred for 30 minutes. A suspension of 30 g of Ser(Bzl)-His(Tos)-Lys(Z)-OBzl (Compound 1) in 300 ml of methylene chloride was added thereto, and stirred at −10° C. for an hour. The precipitates were filtered off. The filtrate was washed with 10% citric acid aqueous solution, saturated saline, sodium bicarbonate aqueous solution, and saturated saline successively, and passed through silica gel and sodium sulfate anhydride columns. The solvent was distilled off, and the residue was dissolved in chloroform. Next, ether was added to precipitate crystals, which were then filtered and dried to obtain 34.9 g of powdery crystals of Z-Gly-Ser(Bzl)-His(Tos)-Lys(Z)-OBzl (Compound 2).

Similarly, the following compounds were obtained.
Z-Sar-Ser(Bzl)-His(Tos)-Lys(Z)-OBzl (Compound 3)
m.p.: 119°–122° C.
TLC: Rf=0.44 (a).
$[α]_D^{28}$ = +1.25° (c=2.0, CHCl$_3$).
IR (KBr, cm$^{-1}$): 3300, 1690, 1630, 1540, 1380, 1170.
NMR (CDCl$_3$): δ=1.0–1.5 (m,6H), 2.39 (s,3H), 2.92 (s,3H), 3.0–3.7 (m,6H), 4.0 (s,2H), 4.1–4.8 (m,3H), 4.46 (s,2H), 5.01 (s,2H), 5.07 (s,2H), 5.09 (s,2H), 7.24 (s,5H), 7.27 (s,15H), 6.8–8.3 (m,10H).
Z-Trp-Ser(Bzl)-His(Tos)-Lys(Z)-OBzl (Compound 4)
m.p.: 134°–139° C.
TLC: Rf=0.61 (c).
$[α]_D^{28}$ = −13.9° (c=2.0, DMF).
IR (KBr, cm$^{-1}$): 3300, 1690, 1660, 1640, 1530, 1380, 1170.
NMR (CDCl$_3$): δ=0.9–1.9 (m,6H), 2.3 (s,3H), 2.7–3.9 (m,8H), 4.0–4.9 (m,4H), 4.28 (s,2H), 5.00 (s,2H), 5.03 (s,4H), 6.7–9.2 (m,37H).

Z-(pyr)-Glu-Ser(Bzl)-His(Tos)-Lys(Z)-OBzl (Compound 5)
m.p.: 154°–156° C.
TLC: Rf=0.63 (c).
$[\alpha]_D^{28} = -6.7°$ (c=2.0, DMF).
IR (KBr, cm$^{-1}$): 3300, 1780, 1725, 1685, 1635.
NMR (CD$_3$COOD): δ=1.1–2.0 (m,6H), 2.2–2.7 (m,4H), 2.38 (s,3H), 2.8–3.3 (m,4H), 3.4–3.8 (m,2H), 4.42 (s,2H), 4.3–5.0 (m,4H), 5.08 (s,2H), 5.12 (s,2H), 5.16 (s,2H), 7.1–8.2 (m,26H).

EXAMPLE 4

A solution of 2.74 g of DCC in 20 ml of methylene chloride was added to a solution of 5.4 g of Z-Tyr(Bzl) in 50 ml of methylene chloride at −10° C., and stirred for 30 minutes. A suspension of 10 g of Compound 1 in 80 ml of methylene chloride was added thereto, and the reaction was effected at −10° C. for 2 hours and 40 minutes. After one ml of acetic acid was added, the precipitated insoluble matter was filtered off. The filtrate was washed with 10% citric acid aqueous solution, saturated saline, 5% sodium bicarbonate aqueous solution, and saturated saline, and passed through silica gel and sodium sulfate anhydride columns. After the solvent was distilled off, the residue was crystallized with ether, washed with ethyl acetate and dried to obtain 13.9 g of white powdery crystals of Z-Tyr(Bzl)-Ser(Bzl)-His(Tos)-Lys(Z)-OBzl (Compound 6).
m.p.: 151°–153° C.
TLC: Rf=0.81 (c), 0.95 (b).
$[\alpha]_D^{25} = -7.05°$ (c=2.0, DMF).
IR (KBr, cm$^{-1}$); 3300, 3030, 2925, 2850, 1730, 1690, 1630, 1515, 1380, 1170.
NMR (DMSO-d$_6$): δ=1.1–1.8 (m,6H), 2.35 (s,3H), 2.6–3.2 (m,6H), 3.5–3.75 (m,2H), 4.0–4.8 (m,4H), 4.46 (s,2H), 4.92 (s,2H), 4.99 (s,2H), 5.02 (s,2H), 5.08 (s,2H), 6.6–8.3 (m,40H).

Similarly, the following compounds were obtained.
Z-Ala-Ser(Bzl)-His(Tos)-Lys(Z)-OBzl (Compound 7)
m.p.: 148°–150° C.
TLC: Rf=0.51 (c), 0.80 (b).
$[\alpha]_D^{28} = -6.9°$ (c=2.0, DMF).
IR (KBr, cm$^{-1}$): 3290, 1735, 1686, 1660, 1630, 1529, 1250, 1165, 696, 675, 589.
NMR (DMSO-d$_6$): δ=0.9–1.9 (m,9H), 2.37 (s,3H), 2.7–3.2 (m,4H), 3.4–3.8 (m,2H), 4.0–4.8 (m,4H), 4.46 (s,2H), 5.02 (s,4H), 5.10 (s.2H), 7.28 (s,5H), 7.31 (s,15H), 6.9–8.4 (m,11H).
Z-D-Ala-Ser(Bzl)-His(Tos)-Lys(Z)-OBzl (Compound 8)
m.p.: 161°–163° C.
TLC: Rf=0.5 (c).
$[\alpha]_D^{25} = -9.5°$ (c=2.0, DMF).
IR (KBr, cm$^{-1}$): 3315, 1723, 1682, 1660, 1632, 1530, 1166, 1100, 697, 678, 585.
NMR (DMSO-d$_6$): δ=0.9–1.9 (m,9H), 2.34 (s,3H), 2.6–3.2 (m,4H), 3.4–3.8 (m,2H), 3.9–4.8 (m,4H), 4.40 (s,2H), 4.98 (s,4H), 5.05 (s,2H), 7.22 (s,5H), 7.26 (s,15H), 6.9–8.4 (m,11H).
Z-Leu-Ser(Bzl)-His(Tos)-Lys(Z)-OBzl (Compound 9)
m.p.: 145°–147° C.
TLC: Rf=0.62 (c).
$[\alpha]_D^{27} = -9.60°$ (c=2.0, DMF).
IR (KBr, cm$^{-1}$): 3270, 3050, 2940, 2915, 2850, 1735, 1685, 1660, 1635.
NMR (CDCl$_3$-CD$_3$COOD): δ=0.75–1.05 (m,6H), 1.05–1.95 (m,9H), 2.38 (s,3H), 2.80–3.25 (m,4H), 3.40–3.80 (m,2H), 4.10–4.90 (m,4H), 4.45 (s,2H), 5.07 (s,2H), 5.10 (s,4H), 7.20 (s,5H), 7.25 (s,15H), 7.10–8.2 (m,6H).
Z-Pro-Ser(Bzl)-His(Tos)-Lys(Z)-OBzl (Compound 10)
m.p.: 134°–139° C.
TLC: Rf=0.61 (c).
$[\alpha]_D^{28} = -13.9°$ (c=2.0, DMF).
IR (KBr, cm$^{-1}$): 3290, 3030, 2930, 2850, 1740, 1710, 1685, 1640, 1540, 1380, 1170.
NMR (DMSO-d$_6$): δ=1.1–2.15 (m,10H), 2.32 (s,3H), 2.6–3.7 (m,8H), 4.0–4.65 (m,6H), 4.95–5.05 (m,6H), 7.1–8.2 (m,30H).

EXAMPLE 5

2.7 g of 1-hydroxybenzotriazole was added to 10.3 g of Z-Gly-Ser(Bzl)-His(Tos)-Lys(Z)-OBzl (Compound 2) dissolved in 150 ml of methylene chloride, and stirred at room temperature for 15 hours. The formed gel was filtered out and washed with ethyl acetate. The filtrate was concentrated and acetone was added to precipitate a solid, which was then combined with the above gel and recrystallized from methanol-acetone to obtain 6.1 g of a colorless powder of Z-Gly-Ser(Bzl)-His-Lys(Z)-OBzl (Compound 11).
m.p.: 171°–175° C.
TLC: Rf=0.53 (b), 0.71 (f), 0.22 (g), 0.17 (h).
$[\alpha]_D^{23} = -5.2°$ (c=0.5, DMF).
IR (KBr, cm$^{-1}$): 3320, 1730, 1680, 1665, 1640, 1620, 1565, 1525.
NMR (CD$_3$COOD): δ=1.2–2.0 (m,6H), 2.9–3.4 (m,4H), 3.5–3.9 (m,2H), 3.92 (s,2H), 4.3–4.9 (m,3H), 4.44 (s,2H), 5.0–5.2 (m,6H), 7.1–7.5 (m,22H).

| Elementary Analysis: (C$_{47}$H$_{53}$O$_{10}$N$_7$) | | | |
|---|---|---|---|
| | C % | H % | N % |
| Calculated | 64.44 | 6.10 | 11.19 |
| Found | 64.18 | 5.92 | 11.22 |

Similarly, the following compound was obtained.
Z-Trp-Ser(Bzl)-His-Lys(Z)-OBzl (Compound 12)
m.p.: 148°–152° C.
TLC: Rf=0.82 (f).
$[\alpha]_D^{28} = -12.6°$ (c=2.0, DMF).
IR (KBr, cm$^{-1}$): 3200, 1690, 1640, 1530.
NMR (CD$_3$OD-CDCL$_3$): δ−1.0–2.0 (m,6H), 2.8–4.0 (m,8H), 4.35 (s,2H), 4.2–4.8 (m,4H), 4.95 (s,2H), 5.02 (s,2H), 5.10 (s,2H), 6.7–7.7 (m,27H).

EXAMPLE 6

52.7 ml of acetic anhydride and 1.1 ml of pyridine were added to 11.0 g of Z-Sar-Ser(Bzl)-His(Tos)-Lys(Z)-OBzl (Compound 3) dissolved in 105 ml of chloroform, and stirred at room temperature overnight. The solvent was distilled off, and the residue was made alkaline solution with sodium bicarbonate aqueous solution. Then, the resultant suspension was extracted with chloroform. The extract was washed with 5% sodium bicarbonate aqueous solution and water, the solvent was distilled off. Thereafter, water was added to form a precipitate, which was filtered out and dried to obtain 8.38 g of a white powder of Z-Sar-Ser(Bzl)-His-Lys(Z)-OBzl (Compound 13).
m.p.: 124°–127° C.
TLC: Rf=0.59 (f).
$[\alpha]_D^{23} = -9.90°$ (c=2.0, DMF).
IR (KBr, cm$^{-1}$): 3300, 1740, 1700, 1685, 1640, 1530.
NMR (CDCl$_3$+CD$_3$COOD): δ−0.9–2.0 (m,6H), 2.94 (s,3H), 2.8–4.0 (m,6H), 4.07 (s,2H), 4.2–4.8 (m,3H), 4.45 (s,2H), 5.02 (s,2H), 5.06 (s,4H), 6.5 (m,1H), 7.0–7.6 (m,21H).

Similarly, the following compounds were obtained.

Z-Ala-Ser(Bzl)-His-Lys(Z)-OBzl (Compound 14)
 m.p.: 170°–172° C.
 TLC: Rf=0.70 (b).
 $[\alpha]_D^{27} = -14.6°$ (c=2.0, AcOH).
 IR (KBr, cm$^{-1}$): 3280, 1740, 1684, 1659, 1643, 1525, 1255, 1175, 1120, 738, 697, 615.
 NMR (CD$_3$COOD): $\delta$=1.0–2.0 (m,9H), 2.8–3.5 (m,4H), 3.5–4.0 (m,2H), 4.1–5.0 (m,4H), 4.46 (s,2H), 5.06 (s,4H), 5.14 (s,2H), 7.0–7.5 (m,21H), 8.4–8.9 (m,1H).

Z-D-Ala-Ser(Bzl)-His-Lys(Z)-OBzl (Compound 15)
 m.p.: 186°–187° C.
 TLC: Rf=0.70 (b).
 $[\alpha]_D^{27} = -10.7°$ (c=2.0, AcOH).
 IR (KBr, cm$^{-1}$): 3270, 1741, 1681, 1662, 1655, 1636, 1529, 1260, 1175, 1124, 735, 698, 613.
 NMR (CD$_3$COOD): $\delta$=1.0–2.0 (m,9H), 2.8–3.5 (m,4H), 3.5–4.0 (m,2H), 4.1–5.0 (m,4H), 4.45 (s,2H), 5.04 (s,4H), 5.12 (s,2H), 7.0–7.6 (m,21H), 8.4–8.9 (m,1H).

Z-Leu-Ser(Bzl)-His-Lys(Z)-OBzl (Compound 16)
 m.p.: 142°–144° C.
 TLC: Rf=0.63 (b).
 $[\alpha]_D^{22} = -11.76°$ (c=1.0, DMF).
 IR (KBr, cm$^{-1}$): 3800, 3050, 2950, 2925, 2865, 1730, 1685, 1660, 1625.
 NMR (CDCl$_3$+CD$_3$OD): $\delta$=0.80–1.05 (m,6H), 1.05–1.90 (m,9H), 2.80–3.20 (m,4H), 3.40–4.00 (m,2H), 4.00–4.75 (m,4H), 4.46 (s,2H), 5.03 (s,4H), 5.09 (s,2H), 6.68 (m,1H), 7.0–7.5 (m,21H).

Z-Tyr(Bzl)-Ser(Bzl)-His-Lys(Z)-OBzl (Compound 17)
 m.p.: 171°–172° C.
 TLC: Rf=0.71 (b).
 $[\alpha]_D^{27} = -5.14°$ (c=2.0,AcOH).
 IR (KBr, cm$^{-1}$): 3275, 3030, 2920, 2850, 1720, 1680, 1635, 1510.
 NMR (CD$_3$COOD): $\delta$=1.2–1.9 (m,6H), 2.8–3.5 (m,6H), 3.5–3.9 (m,2H), 4.52 (s,2H), 4.4–4.9 (m,4H), 5.05–5.18 (s,8H), 6.78–7.5 (m,31H).

Z-Pro-Ser(Bzl)-His-Lys(Z)-OBzl (Compound 18)
 m.p.: 100°–102° C.
 TLC: Rf=0.71 (b).
 $[\alpha]_D^{27} = -26.74°$ (c=2.0, DMF).
 IR (KBr, cm$^{-1}$): 3280, 3030, 2925, 2850, 1730, 1680–1660, 1635.
 NMR (CDCl$_3$): $\delta$=0.6–2.2 (m,10H), 2.75–3.2 (m,4H), 3.2–3.8 (m,4H), 4.2–4.8 (m,6H), 5.05 (s,6H), 5.4–5.6 (m,1H), 6.6–7.4 (m,25H), 8.3–8.5 (m,1H).

Z-(pyr)Glu-Ser(Bzl)-His-Lys(Z)-OBzl (Compound 19)
 m.p.: 120°–123° C.
 TLC: Rf=0.66 (b).
 $[\alpha]_D^{28} = -16.0°$ (c=2.0, DMF).
 IR (KBr, cm$^{-1}$): 3290, 1775, 1685, 1640.
 NMR (CD$_3$OD): $\delta$=1.1–1.9 (m,6H), 2.0–2.7 (m,4H), 2.8–3.2 (m,4H), 3.4–3.9 (m,2H), 4.2–4.8 (m,4H), 4.42 (s,2H), 5.04 (s,2H), 5.10 (s,4H), 6.75 (brs,1H), 7.1–7.5 (m,21H).

EXAMPLE 7

10.5 g of palladium-on-charcoal was added to 23.2 g of Z-Gly-Ser(Bzl)-His-Lys(Z)-OBzl (Compound 11) suspended in a mixed solvent of 160 ml of methanol, 40 ml of acetic acid and 20 ml of water, and stirring was continued under atmospheric pressure in hydrogen atmosphere for 38 hours. After the catalyst was filtered off, the filtrate was washed with water and concentrated. The crude product was dissolved in water and eluted with 0.5N ammonia water using a strongly acidic ion exchange resin (NH$_4$+type). The eluate was concentrated and crystallized to obtain 8.0 g of Gly-Ser-His-Lys (Compound 20).
 m.p.: 119°–121° C.
 TLC: Rf=0.29 (d), 0.48 (e).
 $[\alpha]_D^{26} = -39.4°$ (c=2.0, H$_2$O).
 IR (KBr, cm$^{-1}$): 3700–2000, 1650, 1530, 1390, 1160, 1060, 770, 630.
 NMR (D$_2$O): $\delta$=1.0–2.1 (m,6H), 2.8–3.3 (m,4H), 3.43 (s,2H), 3.83 (d,2H,J=6 Hz), 4.0–4.9 (m,3H), 6.92 (brs.1H), 7.65 (brs,1H).

Similarly, the following compounds were obtained.

Ala-Ser-His-Lys (Compound 21)
 m.p.: 123°–128° C. (dec.).
 TLC: Rf=0.31 (d).
 $[\alpha]_D^{25} = -38.0°$ (c=2.0, H$_2$O).
 IR (KBr, cm$^{-1}$): 3700–2200, 1650, 1395.
 NMR (D$_2$O): $\delta$=1.39 (d,3H, J=7 Hz), 1.1–2.1 (m,6H), 2.8–3.3 (m,4H), 3.62 (q,1H, J=7 Hz), 3.85 (d,2H, J=6 Hz), 4.0–4.9 (m,3H), 6.93 (brs,1H), 7.65 (brs,1H).

D-Ala-Ser-His-Lys (Compound 22)
 m.p.: 129°–133° C.
 TLC: Rf=0.31 (d).
 $[\alpha]_D^{25} = -43.0°$ (c=2.0, H$_2$O).
 IR (KBr, cm$^{-1}$): 3700–2200, 1650, 1395.
 NMR (D$_2$O): $\delta$=1.39 (d,3H, J=7 Hz), 1.1–2.1 (m,6H), 2.8–3.3 (m,4H), 3.62 (q,1H, J=7 Hz), 3.85 (d,2H, J=6 Hz), 4.0–4.9 (m,3H), 6.93 (brs,1H), 7.65 (brs,1H).

Leu-Ser-His-Lys (Compound 23)
 m.p.: Impossible to specify.
 TLC: Rf=0.37 (d).
 $[\alpha]_D^{28} = -27.0°$ (c=2.0, H$_2$O).
 IR (KBr, cm$^{-1}$): 3600–2500, 2940, 1660–1505.
 NMR (D$_2$O): $\delta$=0.89 (d,6H, J=5 Hz), 1.1–2.1 (m,9H), 2.7–3.3 (m,4H), 3.3–3.65 (m,1H), 3.84 (d,2H, J=6 Hz), 3.9–4.6 (m,3H), 6.91 (brs, 1H), 7.62 (brs, 1H).

Tyr-Ser-His-Lys (Compound 24)
 m.p.: 157°–160° C.
 TLC: Rf=0.37 (d).
 $[\alpha]_D^{29} = -15.56°$ (c=2.0, H$_2$O).
 IR (KBr, cm$^{-1}$): 3600–2500, 1650, 1600, 1510.
 NMR (D$_2$O): $\delta$=1.1–2.0 (m,6H), 2.7–3.25 (m,6H), 3.75 (d,2H, J=6 Hz), 3.55–4.7 (m,4H), 6.67–7.10 (m,5H), 7.62 (brs, 1H).

EXAMPLE 8

Similarly as in Example 7, catalytic reduction and purification were effected using a strongly acidic ion exchange resin. The eluate was concentrated, and acetic acid was added. The mixture was stirred, and then concentrated to dryness. The residue was crystallized by adding acetone to obtain Gly-Ser-His-Lys.CH$_3$COOH.H$_2$O (Compound 25).
 m.p.: 126°–132° C. (dec.).
 TLC: Rf=0.29 (d), 0.48 (e).
 $[\alpha]_D^{23} = -30.6°$ (c=2.0, H$_2$O).
 IR (KBr, cm$^{-1}$): 3600–2500, 1680–1500.
 NMR (D$_2$O): $\delta$=1.1–2.1 (m,6H), 1.93 (s,3H), 3.01 (t,2H), 3.18 (d,2H), 3.85 (d,2H), 3.89 (s,2H), 4.0–5.0 (m,3H), 7.11 (d,1H), 8.05 (d,1H).

Elementary Analysis: (as $C_{17}H_{29}O_6N_7 \cdot CH_3COOH \cdot H_2O$)

|  | C % | H % | N % |
|---|---|---|---|
| Calculated | 45.15 | 6.93 | 19.41 |
| Found | 45.43 | 6.79 | 19.58 |

EXAMPLE 9

7.0 g of Z-Sar-Ser(Bzl)-His-Lys(Z)-OBzl (Compound 13) was dissolved in 45 ml of aqueous methanol (MeOH/$H_2O$=2/1), and catalytically hydrogenized in the presence of 3.15 g of 10% palladium-on-charcoal at room temperature for 28 hours. The catalyst was filtered off, and the filtrate was concentrated. After methanol aqueous solution was added to the concentrate, it was eluted with aqueous methanol using a dextran gel column. The eluate was concentrated and the residue was crystallized with acetone to obtain 2.27 g of a white powder of Sar-Ser-His-Lys (Compound 26).

m.p.: 117°-165° C. (Difficult to specify).
TLC: Rf=0.20 (d).
$[\alpha]_D^{26} = -39.5°$ (c=2.0, $H_2O$).
IR (KBr, $cm^{-1}$): 3700-2300, 1660-1520, 1390.
NMR ($D_2O$): δ=1.1-2.1 (m,6H), 2.44 (s,3H), 2.2-3.3 (m,4H), 3.46 (s,2H), 3.90 (d,2H, J=6 Hz), 4.0-4.8 (m,3H), 6.97 (brs,1H), 7.68 (brs,1H).

Similarly, the following compounds were obtained.
Pro-Ser-His-Lys (Compound 27)
m.p.: 130°-140° C.
TLC: Rf=0.30 (d).
$[\alpha]_D^{27} = -58.8°$ (c=2.0, $H_2O$).
IR (KBr, $cm^{-1}$): 3600-2500, 1650, 1580-1560, 1520.
NMR ($D_2O$): δ=1.1-2.1 (m,10H), 2.8-3.4 (m,6H), 3.85 (d,2H, J=6 Hz), 3.9-4.7 (m,3H), 6.9 (d,1H), 7.6 (d,1H).

(pyr)Glu-Ser-His-Lys (Compound 28)
m.p.: 200°-210° C. (dec.).
TLC: Rf=0.33 (d).
$[\alpha]_D^{27} = -42.5°$ (c=2.0, $H_2O$).
IR (KBr, $cm^{-1}$): 3600-2300, 3260, 1650.
NMR ($D_2O$): δ=1.1-2.0 (m,6H), 2.0-2.7 (m,4H), 2.8-3.3 (m,4H), 3.85 (d,2H), J=6 Hz), 4.0-4.8 (m,4H), 6.95 (brs,1H), 7.68 (brs,1H).

Trp-Ser-His-Lys (Compound 29)
m.p.: 140°-185° C. (Difficult to specify) (dec.).
TLC: Rf=0.42 (d).
$[\alpha]_D^{28} = -5.6°$ (c=2.0, $H_2O$).
IR (KBr, $cm^{-1}$): 3600-2300, 1650, 1580, 1530, 1390.
NMR ($D_2O$): δ=1.2-2.1 (m,6H), 2.3-2.7 (m,2H), 2.7-3.4 (m,4H), 3.3-4.7 (m,4H), 3.75 (d,2H, J=6 Hz), 6.8-8.0 (m,7H).

EXAMPLE 10

8.2 g of Z-Leu-Ser(Bzl)-His(Tos)-Lys(Z)-OBzl (Compound 9) and 8 ml of anisole were placed into a HF reaction apparatus, it was reduced in pressure and cooled to −70° C. or below. 85 ml of HF was added, and stirring was effected at 0° C. for an hour. Then, HF was removed. Water was added to the residue, and by-products were removed by extracting with ether. The aqueous layer was subjected to an ion exchange resin, washed with water, and eluted with 0.5N ammonia water. The eluate was concentrated, and the residue was crystallized by adding acetone-ether to obtain 2.9 g of white crystals of Leu-Ser-His-Lys (Compound 23) (The physical data were in agreement with those obtained in Example 7).

EXAMPLE 11

(i) 30 g of Boc-Lys(Z-Cl).t-butylamine was dissolved in 300 ml of water, and cooled with ice. After its pH was adjusted to 4 by adding citric acid aqueous solution, extraction was effected with ethyl acetate, followed by washing and drying. To the obtained Boc-Lys(Z-Cl) were added 47 g of a chloromethylated resin (2% divinylbenzene-polystyrene, Cl content: 1.32 mmole/g), 140 ml of ethanol, 65 ml of chloroform and 7.7 ml of triethylamine. Then the mixture was stirred at room temperature for an hour, and reflux was effected under heating for 48 hours. The resin was filtered, washed with ethanol-acetic acid, methanol and methylene chloride, and dried under reduced pressure to obtain 57 g of Boc-Lys(Z-Cl)-resin.

(ii) 15 g of the Boc-Lys(Z-Cl)-resin was charged into a synthesizing reactor for solid-phase synthesis, and shaking and filtration using methylene chloride were repeated to effect washing and swelling of the resin. It was then debutoxycarbonylated by trifluoroacetic acid in methylen chloride at room temperature for 20 min., washed thoroughly with methylene chloride, then treated with triethylamine for 10 minutes, and further washed with methylene chloride. After a solution of 6.8 g of Boc-His(Tos) in methylene chloride and a solution of 3.4 g of DCC in methylene chloride were added, the mixture was shaken for 2 hours. Washing with methylene chloride and ethanol was effected successively. While checking the degree of completion of condensation by sampling a small quantity of the resin, reactions using 4.9 g of Boc-Ser(Bzl) and 2.9 g of Boc-Gly were repeated to obtain 18.6 g of the resin.

(iii) 9.6 g of the obtained Boc-Gly-Ser(Bzl)-His(Tos)-Lys(Z-Cl)-resin and 9 ml of anisole were charged into a HF reaction apparatus. Thereafter, its pressure was reduced, and it was cooled to −70° C. or below. Next, 90 ml of HF was introduced in it, and the mixture was stirred at 0° C. for an hour. After the HF was distilled off, water was added, followed by stirring. Then, the resin was filtered and washed with water. The filtrate and the washing were combined together, and the aqueous layer was concentrated after washing with ether. The residue was subjected to a strongly acidic ion exchange resin ($NH_4^+$type) and eluted with 0.03N-0.5N ammonia water. Thereafter, procedures similar to those in Example 8 were conducted to obtain Gly-Ser-His-Lys.$CH_3COOH \cdot H_2O$ (Compound 25).

Further, this was treated with TosOH, to obtain Gly-Ser-His-Lys.2TosOH (Compound 30).

m.p.: 184°-188° C. (dec.).
NMR ($D_2O$): δ=1.1-2.1 (m,6H), 2.35 (s,6H), 2.98 (t.2H), 3.21 (d,2H), 3.85 (d,2H), 3.89 (s,2H), 4.0-5.0 (m,3H), 7.30 (d,1H), 7.25-7.85 (m,8H), 8.55 (d,1H).

The pharmacological effects of the peptide compounds of this invention are described below.

1. Acute Toxicity

Peptide compounds of this invention were intravenously administered to mice and the acute toxicity was evaluated from the number of the dead animals after 72 hours.

As the result, the $LD_{50}$ of the peptide compounds of this invention were all higher than 1,500 mg/kg.

2. Histamine-induced Ulcer Inhibiting Effect

Groups each consisting of 10 Wister strain male rats (120-130 g) were starved for 24 hours, and the drug to be tested were intravenously administered (i.v.). Immediately thereafter, according to the method by Bücher et al. [Bücher, F. et al., Beitr. Path. Anat. 81, 391 (1928)], 300 mg/kg of histamine dihydrochloride was administered intraperitoneally (i.p.). Four hours later, each animal was decapitated to bleed, and the stomach was removed. 6 ml of physiological saline was infused into the removed stomach, which was then dipped in 10% formalin for 10 minutes. Then, the stomach was incised along the greater curvature. The ulcer appeared on the stomach mucous membrane was observed on a stereoscopic microscope to measure the surface area of the ulcer lesion, and the total area was designated as the ulcer coefficient.

The results are given in Table 1.

TABLE 1

| Drug to be tested | Dosage (mg/kg) | Ulcer coefficient[b] | Inhibition rate (%) |
|---|---|---|---|
| Control[a] | 2.5 (ml) | 28.4 ± 3.2 | — |
| Compound 20 | 20 | 4.6 ± 0.8 | 83.8 |
| Compound 21 | 20 | 12.2 ± 2.3 | 57.0 |
| Compound 22 | 20 | 13.8 ± 2.9 | 51.4 |
| Compound 23 | 20 | 13.4 ± 3.1 | 52.8 |
| Compound 24 | 20 | 12.9 ± 1.1 | 54.6 |
| Compound 25 | 20 | 5.7 ± 2.6 | 79.9 |
| Compound 26 | 20 | 11.0 ± 1.7 | 61.3 |
| Compound 27 | 20 | 11.3 ± 3.5 | 60.2 |
| Compound 28 | 20 | 12.2 ± 2.6 | 57.0 |
| Compound 29 | 20 | 9.1 ± 2.5 | 68.0 |
| Cimetidine | 25 | 10.9 ± 1.9 | 61.6 |

[a]Physiological saline
[b]mean ± S.E.

3. Pylorus Ligation Ulcer Inhibiting Effect

Groups each consisting of 10 Wister strain male rats were starved for 24 hours, and the pylorus was ligatured under etherized conditions. The peptide compound of this invention (Compound 25) was intraperitoneally administered. Eighteen hours later, the stomach was removed and cut open. The ulcer appeared on the rumen was evaluated using 6-ranked ulcer index according to the method by Narumi et al. [A. Narumi, et al., J. Takeda Res. Lab., 29, 85 (1970)].

The results are given in Table 2.

TABLE 2

| Drug to be tested | Dosage (i.p.) | Ulcer index[b] |
|---|---|---|
| Control (Physiological saline) | 4 ml/kg | 4.5 ± 0.3 |
| Compound 25 | 1 mg/kg | 3.1 ± 0.5 |
| Tissue Respiration Activator[a] | 10 ml/kg | 3.5 ± 0.5 |

[a]Deproteinized extract from calf serum (commercial product)
[b]mean ± S.E. (p < 0.01)

4. The dosages of the peptide compound of this invention which exhibit 50% inhibition against various experimental ulcers ($ID_{50}$) are shown in Table 3 hereinbelow.

The peptide compound of this invention (Compound 25) and cimetidine and atropine both employed as the comparative drugs were intravenously administered.

(A) Experiment or Restraint and Water Immersion Stress Ulcer Inhibiting Effect

According to the method by Takagi et al. [Takagi, K. et al., Chem. Pharm. Bull., 12, 465 (1964)], the effect on the ulcer in rats induced by stress due to restraint and immersing in water in wire cages (25° C., 4 hours) was examined. The drugs to be tested were administered once before loading the stress.

(B) Experiment on Aspirin-Induced Ulcer Inhibiting Effect

According to the method by Brodie et al. [Brodie, D. A. & Chase, B. J., Gastroenterology, 53, 604 (1967)], the drug to be tested was orally administered to rats once before the oral administration of 200 mg/kg of aspirin.

(C) Experiment on Histamine-Induced Ulcer Inhibiting Effect

According to the method by Bücher et al. [ Bücher, F. et al., Beitr. Path. Anat., 81, 391 (1928)], the drug to be tested was intraperitoneally administered to rats once before the oral administration of 300 mg/kg of histamine.

(D) Experiment on Cortisone-Induced Ulcer Inhibiting Effect

According to the method by Robert et al. [Robert, A & Nezamis, J. E., Proc. Soc. Exptl. Biol. Med., 99, 443 (1958)], rats were starved, and 20 mg/kg of cortisone acetate was subcutaneously administered once a day for 4 days to induce ulcer. The drug to be tested was also administered simultaneously with the cortisone acetate once a day for 4 days.

(E) Experiment on Cysteamine-Induced Duodenal Ulcer Inhibiting Effect

According to the method by Robert at al. [Robert, H. et al., Digestion, 11, 199 (1974)], 400 mg/kg of cysteamine hydrochloride was administered to rats to induce duodenal ulcer. The drug to be tested was administered once before the administration of the cysteamine.

TABLE 3

| Drug to be tested | $ID_{50}$ (mg/kg, i.v.) | | | | |
|---|---|---|---|---|---|
| | A | B | C | D | E |
| Compound 25 | 4.2 | 5.0 | 6.0 | 1.85 | 5.0 |
| Cimetidine | 37.0 | 39.0 | 17.0 | 28.0 | 26.0 |
| Atropine | 0.4 | 0.52 | 0.35 | 0.25 | 0.35 |

5. Acetic Acid-Induced Ulcer Inhibiting Effect

The effect of the peptide compound of this invention on chronic ulcer was examined according to the method by Takagi et al. [Takagi, K. et al., Japan J. Pharmacol., 19, 418 (1970)]. That is, 0.025 ml of 30% acetic acid was injected to the stomach serous membrane in rats, and for 10 days thereafter, the peptide compound of this invention (Compound 25) was intravenously administered once a day. Gefarnate and secretin both employed as the comparative drugs were similarly intramuscularly administered (i.m.).

The results are given in Table 4.

TABLE 4

| Drug to be tested | $ID_{50}$ |
|---|---|
| Compound 25 | 1.0 mg/kg, i.v. |
| Gefarnate | 250 mg/kg, i.m. |
| Secretin | >100 U/kg, i.m. |

6. Antithrombotic Effect (I)

Groups each consisting of 10 Wister strain male rats (120–160 g) were administered with the drug to be tested through the tail vein, and 5 minutes later, blood was taken under etherized conditions at a ratio to 3.8% aqueous sodium citrate solution of 1/10. This was centrifugally separated into platelet rich plasma (PRP) and platelet poor plasma (PPP). Using ADP or collagen as the coagulant, the reaction was effected at 37° C. The transmittance of the plasma with the coagulant and drug to be tested was measured using PRP and PPP as the standards, compared with the control, and the percent inhibition was calculated. As the comparative drug, ticlopidine was orally administered.

The results are given in Table 5 and Table 6.

TABLE 5

(Effect on ADP Induced Hemagglutination)

| Drug to be tested | Dosage (mg/kg) | Transmittance[b] | Inhibition Rate (%) |
|---|---|---|---|
| Control[a] | — | 62.9 ± 6.3 | — |
| Compound 20 | 10 | 14.5 ± 6.6 | 76.9 |
| Compound 21 | 10 | 24.3 ± 3.2 | 61.3 |
| Compound 22 | 10 | 24.2 ± 5.3 | 61.5 |
| Compound 23 | 10 | 40.4 ± 7.8 | 35.8 |
| Compound 24 | 10 | 37.5 ± 7.1 | 40.4 |
| Compound 26 | 10 | 17.8 ± 6.8 | 71.7 |
| Compound 27 | 10 | 24.0 ± 11.2 | 61.8 |
| Compound 28 | 10 | 26.5 ± 7.2 | 57.9 |
| Compound 29 | 10 | 31.5 ± 8.6 | 49.2 |
| Thichlopidine | 100 | 41.6 ± 10.4 | 33.9 |

[a]Physiological saline
[b]mean ± S.E.

TABLE 6

(Effect on Collagen Induced Hemagglutination)

| Drug to be tested | Dosage (mg/kg) | Transmittance[b] | Inhibition rate (%) |
|---|---|---|---|
| Control[a] | — | 52.5 ± 7.1 | — |
| Compound 20 | 2.5 | 24.4 ± 6.2 | 53.5 |
| Compound 20 | 10.0 | 16.8 ± 5.4 | 68.0 |
| Compound 25 | 10.0 | 14.8 ± 4.9 | 71.8 |
| Thichlopidine | 100 | 34.6 ± 10.8 | 34.1 |

[a]Physiological saline
[b]mean ± S.E.

7. Antithrombotic Effect (II)

The present pharmacological test was conducted according to the method by T. Umetsu et al. [Thrombosis and Haemostasis, 39, 74–83 (1978)].

Groups each consisting of 10 Wister strain male rats were anesthetized by intraperitoneal administration of 50 mg/kg of sodium pentobarbital. An extracorporeal shunt prepared by connecting cannula polyethylene tubes to both ends of a polyethylene tube into which a silk thread had been inserted was filled with heparin, the both ends were then inserted into the dissected and exposed left jugular vein and right carotid artery. Thereafter, blood circulation was started. The drug to be tested was intravenously administered one minute before the start of blood circulation. Aspirin was orally administered as a comparative drug.

After 20 minute blood circulation, the wet weight of the thrombus coated to the silk thread was weighed, and the inhibition rate was calculated.

The results are given in Table 7.

TABLE 7

| Drug to be tested | Dosage (mg/kg) | Thrombosis wet weight (mg)[b] | Inhibition rate (%) |
|---|---|---|---|
| Control[a] | — | 38.1 ± 3.4 | — |
| Compound 25 | 1 | 27.7 ± 4.0 | 27.3 |
| Compound 25 | 10 | 21.3 ± 3.3 | 44.1 |
| Component Amino Acid[c] | 10 | 40.9 ± 4.1 | −7.3 |
| Aspirin | 100 | 22.3 ± 3.2 | 41.5 |

[a]Physiological saline
[b]mean ± S.E.
[c]Equimolar mixture of Gly, Ser, His and Lys As clear from the above test results, the peptide compounds of this invention have a significant antiulcer effect, and thus are not only therapeutically useful as treating agents for ulcers of peptic organs, e.g. stomach, duodenum etc., aphthous stomatitis, scald, burn etc. but also expected to be useful as antistress agents, sedatives, analgesics etc.

Further, the peptide compounds of this invention exhibit an excellent antithrombotic effect, and therefore, may be applied in prophylaxis or treatment of various diseases caused by the acceleration of platelet aggregation activity, for example, cerebral thrombosis, cerebral infarction, myocardial infarction, pulmonary infarction, arteriosclerosis and other diseases resulting from the thrombus formation, and prophylaxis or treatment of postoperative thrombosis or the thrombus formation in blood dialysis, and further are useful as agents to prevent the aging of the circulation system and vital body, e.g. arteriosclerosis.

The peptide compounds of this invention have in combination the antiulcer effect and antithrombotic effect as described above, and, for example, are useful in prophylaxis and treatment of e.g. ulcers resulting from the reduction in the blood circulating through the mucous membrane, and are believed to act on the vital body as the tissue-impairment preventing factor and tissue-impairment repairing factor. Further, their participation in the autonomic nerve system modulation and immunity modulation mechanisms is also believed.

The peptide compounds of this invention are composed of tetrapeptides, which synthesis is easy, have only a low level of toxicity and are almost free from a risk of side effects, and therefore are of great usefulness as medicine. Although the test data presented in this application relate primarily to rats and mice, the invention is equally applicable to all mammals such as dogs, cats, monkeys, apes and man.

When formulated as pharmaceutical compositions, the peptide compounds of this invention may also be used as pharmaceutically acceptable salts such as salts of acid adduct with e.g. hydrochloric acid, sulfuric acid, nitric acid, hydrobromic acid, phosphoric acid, boric acid, formic acid, acetic acid, oxalic acid, maleic acid, citric acid, tartaric acid, succinic acid, gluconic acid, lactic acid, benzoic acid, p-toluenesulfonic acid etc., or metal salts, of e.g. sodium, lithium etc., and may be formulated into preparations for oral or parenteral administration either alone or in combination with other pharmaceutically active components.

In the case of oral preparations, they may be admixed with an appropriate diluent, such as lactose, refined sugar, starch etc., and further, if necessary, a binder such as crystalline cellulose, starch, a lubricant such as magnesium stearate, and other additives in conventional manner to prepare tablets, capsules, abstracts, powders etc.

Further, the peptide compounds of this invention may be encapsulated into ribosomes prepared from suitable lipids, for example, phospholipids such as lecithin, sphingomyelins, phosphatidyl ethanolamine, phosphatidyl serine etc., cholesterol, phosphatidic acid, dicetyl phosphate, stearylamine etc. to make preparations. These ribosomes may be either of a multi-layer or mono-layer structure, and may also encapsulate stabilizers, buffers etc. if necessary. Still further, the ribosome may be encapsulated in capsules to present capsules.

For parenteral administration, they may be made into injectable aqueous or non-aqueous solutions, suspensions or emulsions, which may contain preservatives, stabilizers, buffers, dissolution aids etc. upon necessity. Further, they may be presented as injectable dried powders for using by dissolving before use, or as suppositories, ointments etc. by mixing with suitable bases.

The peptide compounds of this invention may be suitably employed depending on the disease to be treated, the route of administration etc., and may be usually administered at a dosage level of 50–400 mg for an adult human per day for oral administration, and 1–200 mg, preferably 10–100 mg, for parenteral administration (injections).

Examples of formulations of pharmaceutical compositions containing the peptide compounds of this invention are given below, but they are not limiting.

FORMULATION EXAMPLE 1

Injectable Composition (per ampule)

| Peptide compound of the Invention | 5 mg |
|---|---|
| Injectable distilled water | q.v. |
| Sodium chloride | q.v. |
| Total | 2 ml |

FORMULATION EXAMPLE 2

Tablet (per tablet)

| Peptide of the Invention | 10 mg |
|---|---|
| Lactose | 230 mg |
| Crystalline cellulose | 50 mg |
| Magnesium stearate | 10 mg |
| Total | 300 mg |

What is claimed is:

1. Peptides having the general formula (I):

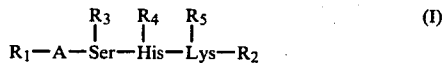

wherein A is a member selected from the group consisting of Gly-, Ala-, D-Ala-, Leu-, Tyr-, Sar-, Pro-, (pyr)-Glu-, Trp-, Val-, Ileu-, Ser-, Thr-, Hyp-, Glu-, Gln-, Asn-, Asp-, Phe-, and DOPA, which may optionally have protecting group; $R_1$ denotes hydrogen atom, lower alkyl group, acyl group, alkoxycarbonyl group, or aralkyloxycarbonyl group which may optionally be substituted with halogen atom, alkoxy group, or nitro group; $R_2$ denotes hydroxy group, alkoxy group, aryloxy group, aralkyloxy group, or amino group which may optionally be substituted with lower alkyl group; $R_3$ denotes hydrogen atom, lower alkyl group, acyl group, or aralkyl group; $R_4$ denotes hydrogen atom, tosyl group, trityl group, aralkyl group, or aralkyloxycarbonyl group which may optionally be substituted with halogen atom, alkoxy group, or nitro group; $R_5$ denotes hydrogen atom, lower alkyl group, acyl group, tosyl group, alkoxycarbonyl group, or aralkyloxycarbonyl group which may optionally be substituted with halogen atom, alkoxyl group, or nitro group, and pharmaceutically acceptable salts thereof.

2. Peptides compound according to claim 1, wherein the peptide compound is in a form of a salt with one selected from the group substantially consisting of hydrochloric acid, sulfuric acid, nitric acid, hydrobromic acid, phosphoric acid, perchloric acid, thiocyanic acid, boroic acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid, sulfanilic acid, sodium, potassium, lithium, calcium, magnesium, and aluminium.

3. Peptide compound according to claim 1, wherein the peptide compound is in a form of a complex of a metal selected from the group substantially consisting of Zn, Ni, Co, Cu and Fe.

4. Gly-Ser-His-Lys.
5. Ala-Ser-His-Lys.
6. D-Ala-Ser-His-Lys.
7. Leu-Ser-His-Lys.
8. Tyr-Ser-His-Lys.
9. Gly-Ser-His-Lys.CH₃COOH.H₂O.
10. Sar-Ser-His-Lys.
11. Pro-Ser-His-Lys.
12. (Pyr)Glu-Ser-His-Lys.
13. Trp-Ser-His-Lys.
14. Gly-Ser-His-Lys.2TosOH.
15. A method for treating mammals suffering from ulcer with at least one of compounds of the formula (I) and pharmaceutically acceptable salts thereof,

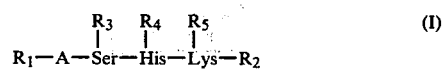

wherein A is a member selected from the group consisting of Gly-, Ala-, D-Ala-, Leu-, Try-, Sar-, Pro-, (pyr)-Glu-, Trp-, Val-, Ileu-, Ser-, Thr-, Hyp-, Glu-, Gln-, Asn-, Asp-, Phe-, and DOPA, which may optionally have a protecting group; $R_1$ is hydrogen atom, lower alkyl group, acyl group, alkoxycarbonyl group or aralkyloxycarbonyl group which may be optionally substituted with halogen atom, alkoxy group or nitro group; $R_2$ is hydroxy group, alkoxy group, aryloxy group, aralkyloxy group or amino group which may be optionally substituted with lower alkyl group; $R_3$ is hydrogen atom, lower alkyl group, acyl group or aralkyl group; $R_4$ is hydrogen atom, tosyl group, trityl group, aralkyl group or aralkyloxycarbonyl group which may be optionally substituted with halogen atom, alkoxy group or nitro group; and $R_5$ is hydrogen atom, lower alkyl group, acyl group, tosyl group, alkoxycarbonyl group or aralkyloxycarbonyl group which may be optionally substituted with halogen atom, alkoxy group or nitro group.

16. Peptides having the general formula (II):

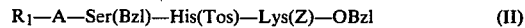

wherein $R_1$ is hydrogen or Z; and A is a residue of an amino acid selected from the group consisting of Gly, Ala, D-Ala, Leu, Tyr(Bzl), Sar, Pro, (pyr)Glu and Trp.

17. Peptides having the general formula (III):

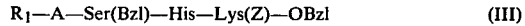

wherein $R_1$ is hydrogen or Z; and A is a residue of an amine acid selected from the group consisting of Gly, Ala, D-Ala, Leu, Tyr(Bzl), Sar, Pro, (pyr)Glu and Trp.

18. Peptides having the general formula (IV):

wherein A is a residue of an amino acid selected from the group consisting of Gly, Ala, D-Ala, Leu, Tyr, Sar, Pro, (pyr)Glu and Trp.

19. A method for treating mammals suffering from thrombus with at least one of compounds of the formula (I) and pharmaceutically acceptable salts thereof,

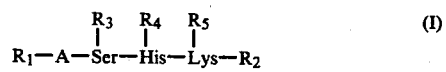

wherein A is a member selected from the group consisting of Gly-, Ala-, D-Ala-, Leu-, Tyr-, Sar-, Pro-, (pyr)Glu-, Trp-, Val-, Ileu-, Ser-, Thr-, Hyp-, Glu-, Gln-, Asn-, Asp-, Phe-, and DOPA, which may optionally have a protecting group; $R_1$ is hydrogen atom, lower alkyl group, acyl group, alkoxycarbonyl group or aralkyloxycarbonyl group which may be optionally substituted with halogen atom, alkoxy group or nitro group; $R_2$ is hydroxy group, alkoxy group, aryloxy group, aralkyloxy group or amino group which may be optionally substituted with lower alkyl group; $R_3$ is hydrogen atom, lower alkyl group, acyl group or aralkyl group; $R_4$ is hydrogen atom, tosyl group, trityl group, aralkyl group or aralkyloxycarbonyl group which may be optionally substituted with halogen atom, alkoxy group or nitro group; and $R_5$ is hydrogen atom, lower alkyl group, acyl group, tosyl group, alkoxycarbonyl group or aralkyloxycarbonyl group which may be optionally substituted with halogen atom, alkoxy group or nitro group.

* * * * *